(12) United States Patent
Wood et al.

(10) Patent No.: US 11,642,080 B2
(45) Date of Patent: *May 9, 2023

(54) PORTABLE HAND-HELD VEIN-IMAGE-ENHANCING DEVICE

(71) Applicant: AccuVein Inc., Cold Spring Harbor, NY (US)

(72) Inventors: Fred Wood, Medford, NY (US); Ron Goldman, Cold Spring Harbor, NY (US); Stephen P. Conlon, Glen Mills, PA (US); Vincent Luciano, Shoreham, NY (US)

(73) Assignee: AccuVein, INC., Medford, NY (US)

( * ) Notice: Subject to any disclaimer, the term of this patent is extended or adjusted under 35 U.S.C. 154(b) by 808 days.

This patent is subject to a terminal disclaimer.

(21) Appl. No.: 16/674,212

(22) Filed: Nov. 5, 2019

(65) Prior Publication Data

US 2020/0114092 A1 Apr. 16, 2020

Related U.S. Application Data

(63) Continuation of application No. 15/096,518, filed on Apr. 12, 2016, now Pat. No. 10,500,350, which is a
(Continued)

(51) Int. Cl.
*A61B 5/00* (2006.01)
*A61M 5/42* (2006.01)
(Continued)

(52) U.S. Cl.
CPC ............ *A61B 5/489* (2013.01); *A61B 5/0059* (2013.01); *A61B 5/0064* (2013.01);
(Continued)

(58) Field of Classification Search
None
See application file for complete search history.

(56) References Cited

U.S. PATENT DOCUMENTS 3,136,310 A 6/1964 Meltzer
3,349,762 A 10/1967 Kapany
(Continued)

FOREIGN PATENT DOCUMENTS

FR 2289149 5/1976
GB 1298707 12/1972
(Continued)

OTHER PUBLICATIONS

Wiklof, Chris, "Display Technology Spawns Laser Camera," LaserFocusWorld, Dec. 1, 2004, vol. 40, Issue 12, PennWell Corp., USA.
Nikbin, Darius, "IPMS Targets Colour Laser Projectors," Optics & Laser Europe, Mar. 1006, Isue 137, p. 11.
(Continued)

*Primary Examiner* — James M Kish
(74) *Attorney, Agent, or Firm* — Thomas A. O'Rourke; Bodner & O'Rourke, LLP

(57) ABSTRACT

It is known in the art to use an apparatus to enhance the visual appearance of the veins and arteries in a patient to facilitate insertion of needles into those veins and arteries. This application discloses a number of inventions that add additional data collection and presentation capabilities to a handheld vein enhancement apparatus and a set of processes for the collection of blood and the delivery of IV medicines that use the handheld device to mediate the process.

16 Claims, 8 Drawing Sheets

Related U.S. Application Data continuation of application No. 13/910,257, filed on Jun. 5, 2013, now Pat. No. 9,345,427, which is a continuation of application No. 11/807,359, filed on May 25, 2007, now Pat. No. 8,489,178, which is a continuation-in-part of application No. 11/700,729, filed on Jan. 31, 2007, now Pat. No. 8,838,210, and a continuation-in-part of application No. 11/478,322, filed on Jun. 29, 2006, now Pat. No. 8,478,386.

(60) Provisional application No. 60/898,506, filed on Jan. 31, 2007, provisional application No. 60/817,623, filed on Jun. 29, 2006, provisional application No. 60/757,704, filed on Jan. 10, 2006.

(51) Int. Cl.
| | | |
|---|---|---|
| *G06V 40/14* | (2022.01) | |
| *A61B 5/15* | (2006.01) | |
| *A61B 90/98* | (2016.01) | |
| *A61B 5/153* | (2006.01) | |
| *A61B 5/1172* | (2016.01) | |
| *A61B 5/1171* | (2016.01) | |
| *A61B 5/024* | (2006.01) | |
| *A61B 90/00* | (2016.01) | |

(52) U.S. Cl.
CPC ........ *A61B 5/0082* (2013.01); *A61B 5/02416* (2013.01); *A61B 5/1172* (2013.01); *A61B 5/1176* (2013.01); *A61B 5/15003* (2013.01); *A61B 5/153* (2013.01); *A61B 5/150343* (2013.01); *A61B 5/150748* (2013.01); *A61B 5/150786* (2013.01); *A61B 5/4839* (2013.01); *A61B 5/72* (2013.01); *A61B 90/98* (2016.02); *A61M 5/427* (2013.01); *G06V 40/14* (2022.01); *A61B 5/024* (2013.01); *A61B 5/7495* (2013.01); *A61B 2090/366* (2016.02); *A61B 2576/00* (2013.01); *A61M 2205/276* (2013.01); *A61M 2205/50* (2013.01); *A61M 2205/52* (2013.01); *A61M 2205/609* (2013.01)

(56) References Cited

U.S. PATENT DOCUMENTS

| | | |
|---|---|---|
| 3,511,227 A | 5/1970 | Johnson |
| 3,527,932 A | 9/1970 | Thomas |
| 3,818,129 A | 6/1974 | Yamamoto |
| 3,984,629 A | 10/1976 | Gorog |
| 4,030,209 A | 6/1977 | Dreiding |
| 4,057,784 A | 11/1977 | Tafoya |
| 4,109,647 A | 8/1978 | Stern et al. |
| 4,162,405 A | 7/1979 | Chance et al. |
| 4,182,322 A | 1/1980 | Miller |
| 4,185,808 A | 1/1980 | Donohoe et al. |
| 4,213,678 A | 7/1980 | Pomerantzeff et al. |
| 4,265,227 A | 5/1981 | Ruge |
| 4,312,357 A | 1/1982 | Andersson et al. |
| 4,315,318 A | 2/1982 | Kato et al. |
| 4,321,930 A | 3/1982 | Jobsis et al. |
| 4,393,366 A | 7/1983 | Hill |
| 4,495,949 A | 1/1985 | Stoller |
| 4,502,075 A | 2/1985 | DeForest et al. |
| 4,510,938 A | 4/1985 | Jobsis et al. |
| 4,536,790 A | 8/1985 | Kruger et al. |
| 4,565,968 A | 1/1986 | Macovski |
| 4,567,896 A | 2/1986 | Barnea et al. |
| 4,576,175 A | 3/1986 | Epstein |
| 4,590,948 A | 3/1986 | Nilsson |
| 4,586,190 A | 4/1986 | Tsuji |
| 4,596,254 A | 6/1986 | Adrian et al. |
| 4,619,249 A | 10/1986 | Landry |
| 4,669,467 A | 6/1987 | Willett et al. |
| 4,697,147 A | 9/1987 | Moran et al. |
| 4,699,149 A | 10/1987 | Rice |
| 4,703,758 A | 11/1987 | Omura |
| 4,766,299 A | 8/1988 | Tierney et al. |
| 4,771,308 A | 9/1988 | Tejima et al. |
| 4,780,919 A | 11/1988 | Harrison |
| 4,799,103 A | 1/1989 | Muckerheide |
| 4,817,622 A | 4/1989 | Pennypacker et al. |
| 4,846,183 A | 7/1989 | Martin |
| 4,861,973 A | 8/1989 | Hellekson et al. |
| 4,862,894 A | 9/1989 | Fujii |
| 4,899,756 A | 2/1990 | Sonek |
| 4,901,019 A | 2/1990 | Wedeen |
| 4,926,867 A | 5/1990 | Kanda et al. |
| RE33,234 E | 6/1990 | Landry |
| 4,938,205 A | 7/1990 | Nudelman |
| 5,074,642 A | 12/1991 | Hicks |
| 5,088,493 A | 2/1992 | Giannini et al. |
| 5,103,497 A | 4/1992 | Hicks |
| 5,146,923 A | 9/1992 | Dhawan |
| 5,174,298 A | 12/1992 | Dolfi et al. |
| 5,184,188 A | 2/1993 | Bull et al. |
| 5,214,458 A | 5/1993 | Kanai |
| 5,222,495 A | 6/1993 | Clarke et al. |
| 5,261,581 A | 11/1993 | Harden, Sr. |
| 5,293,873 A | 3/1994 | Fang |
| 5,339,817 A | 8/1994 | Nilsson |
| 5,371,347 A | 12/1994 | Plesko |
| 5,406,070 A | 4/1995 | Edgar et al. |
| 5,418,546 A | 5/1995 | Nakagakiuchi et al. |
| 5,423,091 A | 6/1995 | Lange |
| 5,436,655 A | 7/1995 | Hiyama et al. |
| 5,445,157 A | 8/1995 | Adachi et al. |
| D362,910 S | 10/1995 | Creaghan |
| 5,485,530 A | 1/1996 | Lakowicz et al. |
| 5,487,740 A | 1/1996 | Sulek et al. |
| 5,494,032 A | 2/1996 | Robinson et al. |
| 5,497,769 A | 3/1996 | Gratton et al. |
| 5,504,316 A | 4/1996 | Bridgelall et al. |
| 5,519,208 A | 5/1996 | Esparza et al. |
| 5,541,820 A | 7/1996 | McLaughlin |
| 5,542,421 A | 8/1996 | Erdman |
| 5,598,842 A | 2/1997 | Ishihara et al. |
| 5,603,328 A | 2/1997 | Zucker et al. |
| 5,608,210 A | 3/1997 | Esparza et al. |
| 5,610,387 A | 3/1997 | Bard et al. |
| 5,625,458 A | 4/1997 | Alfano et al. |
| 5,631,976 A | 5/1997 | Bolle et al. |
| 5,655,530 A | 8/1997 | Messerschmidt |
| 5,678,555 A * | 10/1997 | O'Connell ............... A61B 5/01 600/479 |
| 5,716,796 A | 2/1998 | Bull et al. |
| 5,719,399 A | 2/1998 | Alfano et al. |
| 5,740,801 A | 4/1998 | Branson |
| 5,747,789 A | 5/1998 | Godik |
| 5,756,981 A | 5/1998 | Roustaei et al. |
| 5,758,650 A | 6/1998 | Miller et al. |
| 5,772,593 A | 6/1998 | Hakamata |
| 5,787,185 A | 7/1998 | Clayden |
| 5,814,040 A | 9/1998 | Nelson et al. |
| 5,836,877 A | 11/1998 | Zavislan |
| 5,847,394 A | 12/1998 | Alfano et al. |
| 5,860,967 A | 1/1999 | Zavislan et al. |
| 5,929,443 A | 7/1999 | Alfano et al. |
| 5,946,220 A | 8/1999 | Lemelson |
| 5,947,906 A | 9/1999 | Dawson, Jr. et al. |
| 5,966,204 A | 10/1999 | Abe |
| 5,966,230 A | 10/1999 | Swartz et al. |
| 5,969,754 A | 10/1999 | Zeman |
| 5,982,553 A | 11/1999 | Bloom et al. |
| 5,988,817 A | 11/1999 | Mizushima et al. |
| 5,995,856 A | 11/1999 | Mannheimer et al. |
| 5,995,866 A | 11/1999 | Lemelson |
| 6,006,126 A | 12/1999 | Cosman |
| 6,032,070 A | 2/2000 | Flock et al. |
| 6,056,692 A | 5/2000 | Schwartz |
| 6,061,583 A | 5/2000 | Ishihara et al. |
| 6,083,486 A | 7/2000 | Weissleder et al. |
| 6,101,036 A | 8/2000 | Bloom |

(56) References Cited

U.S. PATENT DOCUMENTS

| | | |
|---|---|---|
| 6,113,536 A | 9/2000 | Aboul-Hosn et al. |
| 6,122,042 A | 9/2000 | Wunderman et al. |
| 6,132,379 A | 10/2000 | Patacsil et al. |
| 6,135,599 A | 10/2000 | Fang |
| 6,141,985 A | 11/2000 | Cluzeau et al. |
| 6,142,650 A | 11/2000 | Brown et al. |
| 6,149,061 A | 11/2000 | Massieu et al. |
| 6,149,644 A | 11/2000 | Xie |
| 6,171,301 B1 | 1/2001 | Nelson et al. |
| 6,178,340 B1 | 1/2001 | Svetliza |
| 6,179,260 B1 | 1/2001 | Ohanian |
| 6,230,046 B1 | 5/2001 | Crane et al. |
| 6,240,309 B1 | 5/2001 | Yamashita et al. |
| 6,251,073 B1 | 6/2001 | Imran et al. |
| 6,263,227 B1 | 7/2001 | Boggett et al. |
| 6,272,376 B1 | 8/2001 | Marcu et al. |
| 6,301,375 B1 | 10/2001 | Choi |
| 6,305,804 B1 | 10/2001 | Rice et al. |
| 6,314,311 B1 | 11/2001 | Williams et al. |
| 6,334,850 B1 | 1/2002 | Amano et al. |
| 6,353,753 B1 | 3/2002 | Flock et al. |
| 6,424,858 B1 | 7/2002 | Williams |
| 6,436,655 B1 | 8/2002 | Bull et al. |
| 6,438,396 B1 | 8/2002 | Cook et al. |
| 6,463,309 B1 | 10/2002 | Ilia |
| 6,464,646 B1 | 10/2002 | Shalom et al. |
| 6,523,955 B1 | 2/2003 | Eberl et al. |
| 6,542,246 B1 | 4/2003 | Toida |
| 6,556,854 B1 | 4/2003 | Sato et al. |
| 6,556,858 B1 | 4/2003 | Zeman |
| 6,599,247 B1 | 7/2003 | Stetten |
| 6,631,286 B2 | 10/2003 | Pfeiffer et al. |
| 6,648,227 B2 | 11/2003 | Swartz et al. |
| 6,650,916 B2 | 11/2003 | Cook et al. |
| 6,689,075 B2 | 2/2004 | West |
| 6,690,964 B2 | 2/2004 | Bieger et al. |
| 6,702,749 B2 | 3/2004 | Paladini et al. |
| 6,719,257 B1 | 4/2004 | Greene et al. |
| 6,755,789 B2 | 6/2004 | Stringer et al. |
| 6,777,199 B2 | 8/2004 | Bull et al. |
| 6,782,161 B2 | 8/2004 | Barolet et al. |
| 6,845,190 B1 | 1/2005 | Smithwick et al. |
| 6,882,875 B1 | 4/2005 | Crowley |
| 6,889,075 B2 | 5/2005 | Marchitto et al. |
| 6,913,202 B2 | 7/2005 | Tsikos et al. |
| 6,923,762 B1 | 8/2005 | Creaghan, Jr. |
| 6,980,852 B2 | 12/2005 | Jersey-Willuhn et al. |
| 7,092,087 B2 | 8/2006 | Kumar et al. |
| 7,113,817 B1 | 9/2006 | Winchester, Jr. et al. |
| 7,158,660 B2 | 1/2007 | Gee, Jr. et al. |
| 7,158,859 B2 | 1/2007 | Wang et al. |
| 7,204,424 B2 | 4/2007 | Yavid et al. |
| 7,225,005 B2 | 5/2007 | Kaufman et al. |
| 7,227,611 B2 | 6/2007 | Hull et al. |
| 7,239,909 B2 | 7/2007 | Zeman |
| 7,247,832 B2 | 7/2007 | Webb |
| 7,280,860 B2 | 10/2007 | Ikeda et al. |
| 7,283,181 B2 | 10/2007 | Allen et al. |
| 7,302,174 B2 | 11/2007 | Tan et al. |
| 7,333,213 B2 | 2/2008 | Kempe |
| D566,283 S | 4/2008 | Brafford et al. |
| 7,359,531 B2 | 4/2008 | Endoh et al. |
| 7,376,456 B2 | 5/2008 | Marshik-Geurts et al. |
| 7,428,997 B2 | 9/2008 | Wiklof et al. |
| 7,431,695 B1 | 10/2008 | Creaghan |
| 7,448,995 B2 | 11/2008 | Wiklof et al. |
| 7,532,746 B2 | 5/2009 | Marcotte et al. |
| 7,545,837 B2 | 6/2009 | Oka |
| 7,559,895 B2 | 7/2009 | Stetten et al. |
| 7,579,592 B2 | 8/2009 | Kaushal |
| 7,608,057 B2 | 10/2009 | Woehr et al. |
| 7,699,776 B2 | 4/2010 | Walker et al. |
| 7,708,695 B2 | 5/2010 | Akkermans et al. |
| 7,792,334 B2 | 9/2010 | Cohen et al. |
| 7,846,103 B2 | 12/2010 | Cannon, Jr. et al. |
| 7,848,103 B2 | 12/2010 | Zhan |
| 7,904,138 B2 | 3/2011 | Goldman et al. |
| 7,904,139 B2 | 3/2011 | Chance |
| 7,925,332 B2 | 4/2011 | Crane et al. |
| 7,966,051 B2 | 6/2011 | Xie et al. |
| 8,032,205 B2 | 10/2011 | Mullani |
| 8,078,263 B2 | 12/2011 | Zeman et al. |
| 8,187,189 B2 | 5/2012 | Jung et al. |
| 8,199,189 B2 | 6/2012 | Kagenow et al. |
| 8,320,998 B2 | 11/2012 | Sato |
| 8,336,839 B2 | 12/2012 | Boccoleri et al. |
| 8,364,246 B2 | 1/2013 | Thierman |
| 8,467,855 B2 | 6/2013 | Yasui |
| 8,480,662 B2 | 7/2013 | Stolen et al. |
| 8,494,616 B2 | 7/2013 | Zeman |
| 8,498,694 B2 | 7/2013 | McGuire, Jr. et al. |
| 8,509,495 B2 | 8/2013 | Xu et al. |
| 8,537,203 B2 | 9/2013 | Seibel et al. |
| 8,548,572 B2 | 10/2013 | Crane |
| 8,630,465 B2 | 1/2014 | Wieringa et al. |
| 8,649,848 B2 | 2/2014 | Crane et al. |
| 2001/0006426 A1 | 7/2001 | Son et al. |
| 2001/0056237 A1 | 12/2001 | Cane et al. |
| 2002/0016533 A1* | 2/2002 | Marchitto ............ A61B 5/0071 600/310 |
| 2002/0111546 A1 | 8/2002 | Cook |
| 2002/0118338 A1 | 8/2002 | Kohayakawa |
| 2002/0188203 A1 | 12/2002 | Smith et al. |
| 2003/0018271 A1 | 1/2003 | Kimble |
| 2003/0037375 A1 | 2/2003 | Riley et al. |
| 2003/0052105 A1 | 3/2003 | Nagano et al. |
| 2003/0120154 A1 | 6/2003 | Sauer et al. |
| 2003/0125629 A1 | 7/2003 | Ustuner |
| 2003/0156260 A1 | 8/2003 | Putilin et al. |
| 2004/0015062 A1 | 1/2004 | Ntziachristos et al. |
| 2004/0015158 A1 | 1/2004 | Chen et al. |
| 2004/0022421 A1 | 2/2004 | Endoh et al. |
| 2004/0046031 A1 | 3/2004 | Knowles et al. |
| 2004/0071322 A1* | 4/2004 | Choshi .................. A61B 5/489 382/115 |
| 2004/0171923 A1 | 9/2004 | Kalafut et al. |
| 2004/0186357 A1* | 9/2004 | Soderberg ............ G16H 30/20 600/300 |
| 2004/0222301 A1 | 11/2004 | Willins et al. |
| 2004/0237051 A1 | 11/2004 | Clauson |
| 2005/0017924 A1 | 1/2005 | Utt et al. |
| 2005/0033145 A1 | 2/2005 | Graham et al. |
| 2005/0043596 A1 | 2/2005 | Chance |
| 2005/0047134 A1 | 3/2005 | Mueller et al. |
| 2005/0085732 A1 | 4/2005 | Sevick-Muraca et al. |
| 2005/0085802 A1 | 4/2005 | Gruzdev et al. |
| 2005/0113650 A1 | 5/2005 | Pacione et al. |
| 2005/0131291 A1 | 6/2005 | Floyd et al. |
| 2005/0135102 A1 | 6/2005 | Gardiner et al. |
| 2005/0141069 A1 | 6/2005 | Wood et al. |
| 2005/0143662 A1 | 6/2005 | Marchitto et al. |
| 2005/0146765 A1 | 7/2005 | Turner et al. |
| 2005/0154303 A1 | 7/2005 | Walker et al. |
| 2005/0157939 A1 | 7/2005 | Arsenault et al. |
| 2005/0161051 A1 | 7/2005 | Pankratov et al. |
| 2005/0168980 A1 | 8/2005 | Dryden et al. |
| 2005/0174777 A1 | 8/2005 | Cooper et al. |
| 2005/0175048 A1 | 8/2005 | Stern et al. |
| 2005/0187477 A1 | 8/2005 | Serov et al. |
| 2005/0215875 A1 | 9/2005 | Khou |
| 2005/0265586 A1 | 12/2005 | Rowe et al. |
| 2005/0281445 A1 | 12/2005 | Marcotte et al. |
| 2006/0007134 A1 | 1/2006 | Ting |
| 2006/0020212 A1 | 1/2006 | Xu et al. |
| 2006/0025679 A1 | 2/2006 | Viswanathan et al. |
| 2006/0052690 A1 | 3/2006 | Sirohey et al. |
| 2006/0081252 A1 | 4/2006 | Wood |
| 2006/0100523 A1 | 5/2006 | Ogle et al. |
| 2006/0103811 A1 | 5/2006 | May et al. |
| 2006/0122515 A1 | 6/2006 | Zeman et al. |
| 2006/0129037 A1 | 6/2006 | Kaufman et al. |
| 2006/0129038 A1 | 6/2006 | Zelenchuk et al. |
| 2006/0151449 A1 | 7/2006 | Warner, Jr. et al. |
| 2006/0173351 A1 | 8/2006 | Marcotte et al. |

(56) References Cited

U.S. PATENT DOCUMENTS

| | | |
|---|---|---|
| 2006/0184040 A1 | 8/2006 | Keller et al. |
| 2006/0206027 A1 | 9/2006 | Malone |
| 2006/0232660 A1 | 10/2006 | Nakajima et al. |
| 2006/0253010 A1 | 11/2006 | Brady et al. |
| 2006/0271028 A1 | 11/2006 | Altshuler et al. |
| 2006/0276712 A1 | 12/2006 | Stothers |
| 2007/0015980 A1 | 1/2007 | Numada et al. |
| 2007/0016079 A1 | 1/2007 | Freeman et al. |
| 2007/0070302 A1 | 3/2007 | Govorkov et al. |
| 2007/0115435 A1 | 5/2007 | Rosendaal |
| 2007/0129634 A1 | 6/2007 | Hickey et al. |
| 2007/0176851 A1 | 8/2007 | Willey et al. |
| 2007/0238957 A1 | 10/2007 | Yared |
| 2008/0045841 A1 | 2/2008 | Wood et al. |
| 2008/0147147 A1 | 6/2008 | Griffiths et al. |
| 2008/0194930 A1 | 8/2008 | Harris et al. |
| 2008/0214940 A1 | 9/2008 | Benaron |
| 2009/0018414 A1 | 1/2009 | Toofan |
| 2009/0082629 A1 | 3/2009 | Dotan |
| 2009/0171205 A1 | 7/2009 | Kharin et al. |
| 2010/0051808 A1 | 3/2010 | Zeman et al. |
| 2010/0061598 A1 | 3/2010 | Seo |
| 2010/0087787 A1 | 4/2010 | Woehr et al. |
| 2010/0177184 A1 | 7/2010 | Berryhill et al. |
| 2010/0312120 A1 | 12/2010 | Meier |
| 2011/0275932 A1 | 11/2011 | Leblond et al. |
| 2013/0147916 A1 | 6/2013 | Bennett et al. |
| 2014/0039309 A1 | 2/2014 | Harris et al. |
| 2014/0046291 A1 | 2/2014 | Harris et al. |
| 2014/0194747 A1 | 7/2014 | Kruglick |

FOREIGN PATENT DOCUMENTS

| | | |
|---|---|---|
| GB | 1507329 | 4/1978 |
| JP | S60-108043 A | 6/1985 |
| JP | 04-042944 | 2/1992 |
| JP | 07-255847 | 10/1995 |
| JP | 08-023501 A | 1/1996 |
| JP | 08-164123 | 6/1996 |
| JP | 2000-316866 A | 11/2000 |
| JP | 2002-328428 A | 11/2002 |
| JP | 2002-345953 A | 12/2002 |
| JP | 2004-237051 | 8/2004 |
| JP | 2004-329786 A | 11/2004 |
| JP | 2006-102360 | 4/2006 |
| KR | 2003-0020152 A | 3/2003 |
| WO | WO 1994 22370 | 10/1994 |
| WO | WO 1996 39925 | 12/1996 |
| WO | WO 1998 26583 | 6/1998 |
| WO | WO 1999 48420 | 9/1999 |
| WO | WO 2001-82786 | 11/2001 |
| WO | WO 2003-009750 | 2/2003 |
| WO | WO 2005-053773 | 6/2005 |
| WO | WO 2007-078447 | 7/2007 |

OTHER PUBLICATIONS http://sciencegeekgirl.wordpress.com/category/science-myths/page/2/ Myth 7: Blood is Blue.

http://www.exploratorium.edu/sports/hnds_up/hands6.html "Hands Up! To Do & Notice: Getting the Feel of Your Hand".

http://www.wikihow.com/See-Blook-Veins-in-Your-Hand-With-a-Flashlight "How to See Blood Veins in Your Hand With a Flashlight".

* cited by examiner

[1100]  Next    OK    bp:110/50

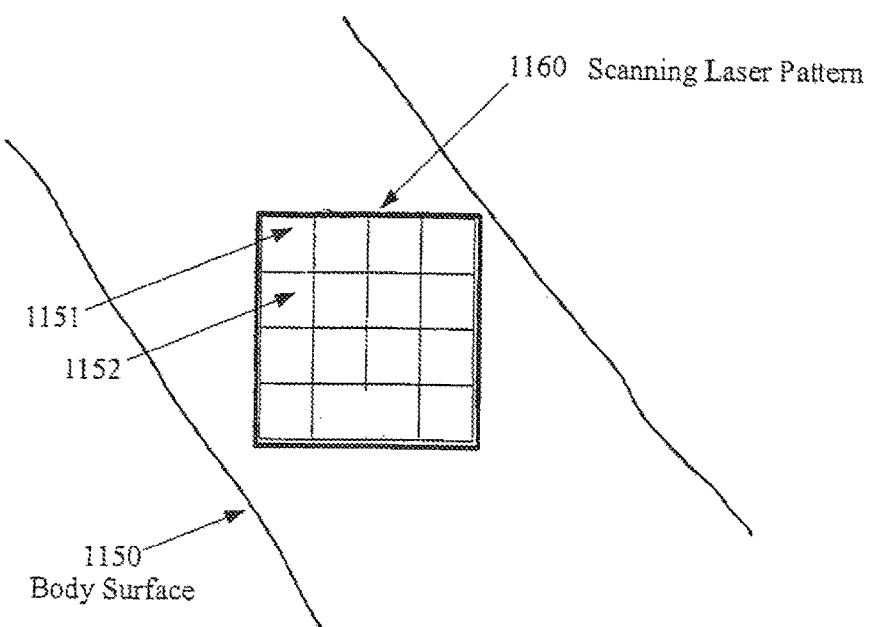
Figure 6a
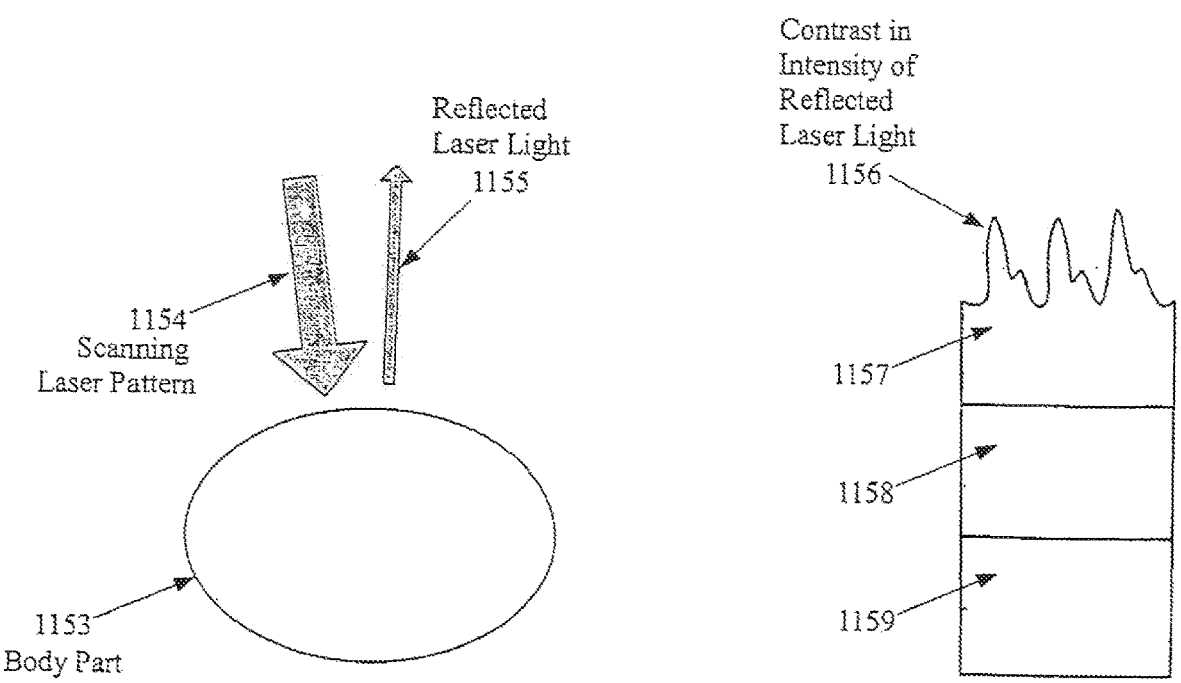
Figure 6b
Figure 6c

PORTABLE HAND-HELD VEIN-IMAGE-ENHANCING DEVICE

CROSS REFERENCE TO RELATED APPLICATIONS

This application is a continuation of U.S. patent application Ser. No. 15/096,518, which is a continuation of U.S. patent application Ser. No. 13/910,257, now issued as U.S. Pat. No. 9,345,427, which is a continuation of U.S. patent application Ser. No. 11/807,359, now issued as U.S. Pat. No. 8,489,178, which claims priority on U.S. Provisional Patent Application Ser. No. 60/898,506, filed Jan. 31, 2007, and on U.S. Provisional Patent Application Ser. No. 60/817,623 filed Jun. 29, 2006, and which parent application is also a continuation-in-part of U.S. patent application Ser. No. 11/700,729 filed Jan. 31, 2007, and U.S. patent application Ser. No. 11/478,322, filed on Jun. 29, 2006. The disclosures of each of these applications are incorporated herein by reference.

FIELD OF INVENTION

In these applications, technology, embodiments and ergonomics of a miniature vein enhancement system is described that uses scanned lasers and other light sources to accomplish the acquisition and projection of a vein pattern to aid the user in locating a vein for venipuncture. In this application, additional capabilities and how these capabilities improve the processes associated with venipuncture are set forth.

Key among these is the use of enhanced embodiments that allow additional data collection and application processes that are critical to the successful performance of venipuncture and related medical and business procedures.

BACKGROUND OF THE INVENTION

It is known in the art to use an apparatus to enhance the visual appearance of the veins and arteries in a patient to facilitate insertion of needles into those veins and arteries. Such a system is described in U.S. Pat. Nos. 5,969,754 and 6,556,858 incorporated herein by reference as well as a paper by Zeman, H. D. et al., "The Clinical Evaluation of Vein Contrast Enhancement", Department of Biomedical Engineering, University of Tennessee Health Science Center, Memphis, Tenn. 8 Feb. 2007. Luminetx is currently marketing such a device under the name "Veinviewer Imaging System" and other information related thereto is available on their website, www.luminetx.com, which is incorporated herein by reference.

In this application, the use of biometrics to identify the user and/or the patient to aid in the management and safety of processes involving venipuncture are described. One such biometric that is unique to this field is to use vein patterns to identify the individual. For example, U.S. Pat. No. 5,787,185, provides for "A method of verifying the identity of an individual comprises capturing an image of the subcutaneous vein pattern at a predetermined region of the individual, converting the captured image to a plurality of stored values representative of the intensity of said image at specified relative locations, processing the stored values to produce a second plurality of stored values representative of the image of the vein pattern having enhanced contrast and subjecting the second plurality of stored values to a thresholding process to select those above a predetermined value and storing a set of measurements derived from the selected ones of said second plurality of stored values for comparison with a corresponding set of measurements made on the individual."

Current embodiments are large, fixed mounted devices. The present invention allows this capability to be integrated into a handheld device as well as to be used as part of the management of the venipuncture process and the handling of delivered drugs and drawn blood.

OBJECTS OF THE INVENTION

1) It is an object of the invention to integrate data collection capabilities such as bar code decoding and biometrics and use those to control the use of the vein scanner 2) It is another object of the invention to combine the projection of vein patterns with the projection of data such as text and/or icons to enhance the usability and capabilities of the device 3) It is another object of the invention to project variable data overlaid on the vein pattern.

4) It is yet another object of the invention to enable payment schemes such that the practitioner can acquire the device at a reduced initial cost and pay per use or pay per user.

5) It is yet another object of the invention to gather and then project back on the patient additional parameters of the patient such as pulse and temperature.

6) It is yet another object of the invention to connect the scanner to a host computer to allow data collected to be stored for future uses such as patient history and billing through wired or wireless means.

7) It is yet another object of the invention to connect to other devices monitoring the patient and to project the data from those monitors back on to the patient.

8) It is yet another object of the invention to project the data collected by the invention and other devices onto an arbitrary surface so that the practitioner can view the data.

9) It is yet another object of the invention to allow the practitioner to avoid blood vessels when performing a procedure on a patient.

10) It is yet another object of this invention to vary the resolution over the working area to allow certain portions of the viewed area to be scanned in higher resolutions than in other areas thereby using the limited bandwidth of the device in an optimized manner.

11) It is yet another object of the invention to provide additional lighting on the working area to aid the practitioner to see the patient's body.

12) It is yet another object of the invention to provide a mechanism for measuring pulse and projecting the pulse rate back on to the body.

13) It is yet another object of the invention to provide a mechanism for measuring blood oxygen levels and projecting the value back on to the body.

14) It is yet another object of the invention to provide a mechanism for reading pulse rate without body contact when the target person is participating in exercise.

15) It is yet another object of the invention to provide the ability for a remote practitioner to perform or assist in the performance of a venipuncture.

SUMMARY OF THE INVENTION

In this application a handheld vein detection device is described with capabilities that allow it to enhance the management of venipuncture processes including blood draw, venous or arterial injection or intravenous starts through the use of bar codes and biometrics; as well as embodiments that enhance usability; and the ability to detect and record additional data about the patient such as the location of venous valves, diagnostic data and re-project that data on to the patient's body.

BRIEF DESCRIPTION OF DRAWINGS

FIG. 6A—this drawing shows d body surface being illuminated by a scanning laser pattern.

FIG. 6B—this drawing shows a part of a body being illuminated by a scanning laser pattern, and with portions of the laser light reflected and absorbed off different structures.

FIG. 6C—this drawing shows a contrast in intensity of reflected laser light.

DETAILED DESCRIPTION OF THE INVENTION

Text and Iconography Projection

The preferred embodiment of the invention simultaneously captures information about the target part of the body (e.g., forearm) such as vein location and then re-projects information about the captured image directly over that area of capture. As previously described, in one embodiment a visible representation of the vein position(s) is projected directly on the vein locations thereby highlighting the veins and making them easier for the practitioner to find.

In enhanced embodiments, digital information in the form of text and/or icons can be included in the information that is re-projected on to the skin. The text and icons can be any useful information to assist the practitioner in performing the procedure. This information may be real time information such as vein depth or it may be patient information such as patient name or it may be mistake proofing information such as the quantity of blood needed to be drawn next so that the vial size can be verified.

Figure 4:
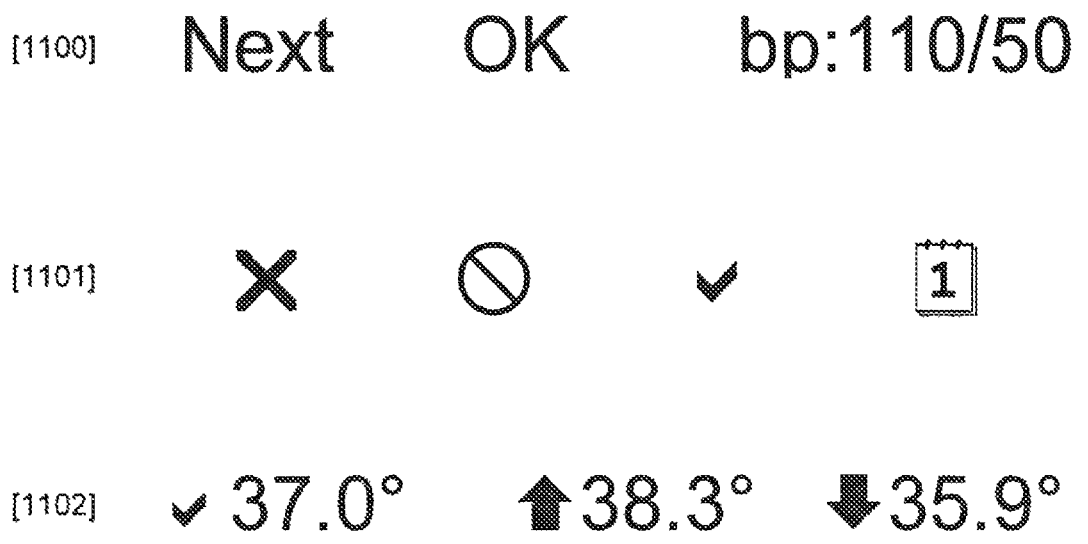

Referring to FIG. 4, text 1100 is projected that indicates information about the process being performed (e.g., next), the status of the system (e.g., OK) or attribute of the patient (e.g., blood pressure is 110/50). As a further enhancement, icons or pictographs 1101 can be projected that shows information in a graphical manner such that it doesn't require a common language between users. Further extending the capabilities, combinations of text and icons 1102 can be projected that show both a specific value for a piece of data and a qualitative indication of the importance of the data. In the example 1102, normal temperature is checked, and high and low temperatures are similarly indicated.

Figure 5:
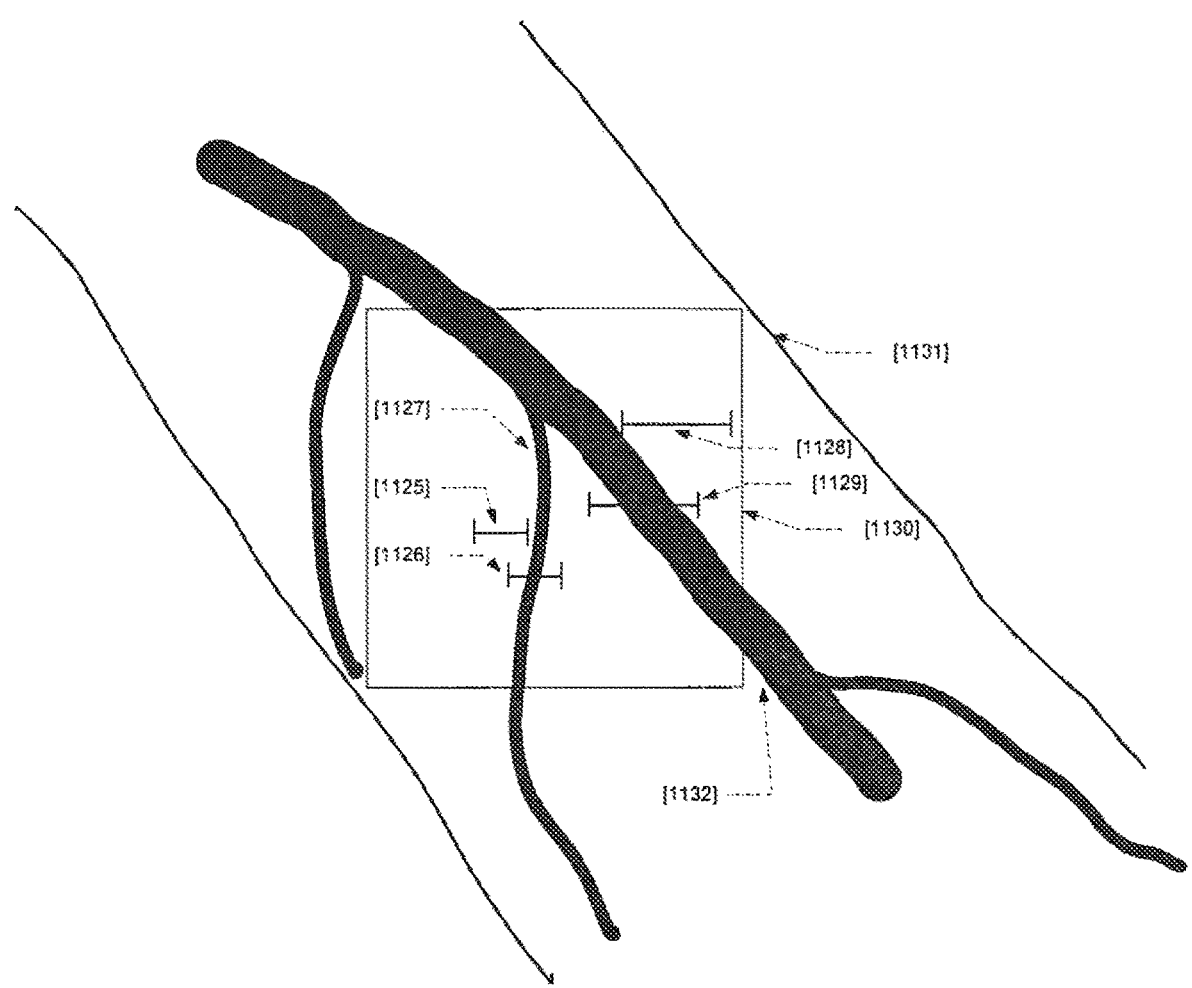
FIG. 5—this drawing shows how variable data can be projected to increase the amount of data available to the practitioner.

An alternative embodiment uses variable markings to indicate some value about the patient's status. In FIG. 5, an arm 1131 is shown with several veins 1127/1132 shown. The projection area 1130 overlaps two veins which are therefore highlighted so that the practitioner can easily find them. Additional information about those veins such as depth can be shown with size indicators 1125/1126/1128/1129. The size of the line between the end marks can be varied to show relative or absolute depth of the vein. If additional colors or intensities are available in the embodiment, the line can be directly overlaid on the vein track 1128/1129 in a different color or in a different intensity or both. Alternatively, a negative image in relation to the projection image can be used to show the size bars 1128/1129. A further alternative would be to place the size bars in proximity but not on top of the imaged veins 1125/1128.

Blood Sample Lifecycle Management

Figure 1:
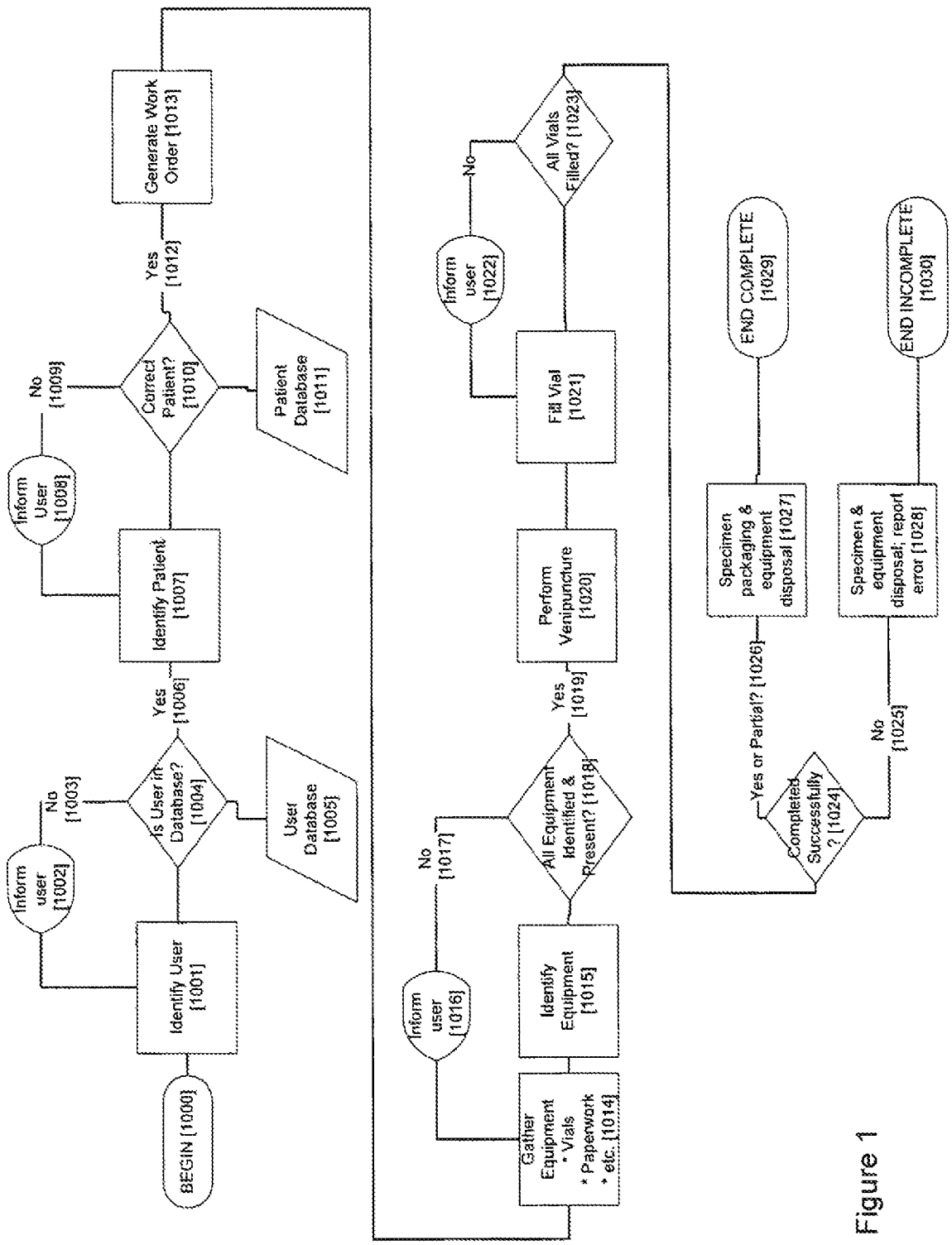
FIG. 1—this flowchart describes the process for taking blood samples using an embodiment of the invention that combines vein location with other data collection including biometrics and bar code scanning.

The process of obtaining blood, storing it, transporting it, testing it and returning the test results has many steps, involves multiple persons and is prone to errors. Through the use of the invention many of these mistakes can be eliminated. Referring to FIG. 1, a process for drawing blood samples is described. The process begins 1000 with the verification of the user/practitioner 1001. This verification can take many forms. The device can be equipped with a keypad such that the user can enter in a personal identifier such as employee id along with an optional pass code. The device can also have a built in token reader such as a smart card reader or an RFID reader such that the user presents this physical token to the device to identify themselves. The device can have built-in biometrics reading capabilities such as a fingerprint reader or an audio input subsystem to allow for voice recognition. Since the device is inherently an image capturing system, image based biometrics such as vein pattern recognition and facial recognition can be used. In most cases a single identifier would be used. However, in some circumstances, a higher level of security might be desired and combinations of identifiers could be used before the process is allowed to continue.

Once an identifier or identifiers have been acquired 1001, they can be compared to a database 1005 of valid users of the device either in a locally stored database or in the case of a scanner that is connected either wired or wirelessly, a remote database can be queried. If the user isn't found in the database 1003 or if the user does not have appropriate training or privileges for the procedure they can be prompted to try again 1002. This prompt could be in a display built into the device, through audio feedback, through visual feedback of an indicator such as an LED, or in the preferred embodiment, through the projection of text or icons from the scanner's projection field. If they user has been successfully identified 1006 then the process moves on to verifying that the patient is the correct patient.

Verification of the patient 1007 can take all of the forms described above for the user of the device. In addition, it is common in hospital environments for a patient to wear a bar coded wrist band. The device can be used to scan that wrist band as a means of identifying the patient. Once an identifier or identifiers have been acquired 1010, they can be compared to a database 1011 of valid patients of the device either in a locally stored database or in the case of a scanner that is connected either wired or wirelessly, a remote database can be queried. If the patient isn't found in the database 1011 or if there are not orders on file for the procedure, the user can be prompted to try again or to correct the situation 1008. This prompt could be in a display built into the device, through audio feedback, through visual feedback of an indicator such as an LED, or in the preferred embodiment, through the projection of text or icons from the scanner's projection field.

Now that the practitioner and the patient have been validated, a list of blood needed and the equipment needed to perform the procedure 1013 can be presented to the user through one of the modalities described above.

Since the invention can be used for bar code data collection, it can be used to ensure that the appropriate materials are in hand before the venipuncture is performed. As the user selects each piece of equipment 1014 they can use bar code or other means of identification such as RFID to verify that the item 1015 is on the list of needed equipment. The process repeats and prompts the user 1016 to continue with gathering equipment until all of the equipment has been identified 1018.

Once a complete set of equipment has been verified 1019, the user can use the vein scanner to find a vein and perform the venipuncture 1020. As the user fills the vials 1021 they can be identified again as filled and if all of the required vials have not been filled 1023, the user can be prompted to continue 1022.

Once all of the vials are filled 1080 the user verifies that the process has completed successfully 1075 and then packages the specimens taken for delivery to the lab 1027/1028 and. The status of the completed process is reported either in the documents forwarded on with the specimens and in a preferred embodiment, this information can be updated in to the medical records database using one of the input and connectivity modalities previously described.

The flowchart and the associated descriptions are shown to highlight how additional input and output modalities integrated into the vein scanner can be used to enhance the process of blood collection. However, the specifics of the processes implemented in different medical environments will require changes to the process flow to meet the unique requirements of the specific environment.

Injection Lifecycle Management

Improper or mistaken delivery of medicines is one of the leading causes of accidental injury or death in the healthcare system. In addition to the use of the vein scanner to help identify the position of veins to aid in the taking of blood specimens, the vein scanner can be used to assist in the delivery of medicines into the patient.

Figure 2:
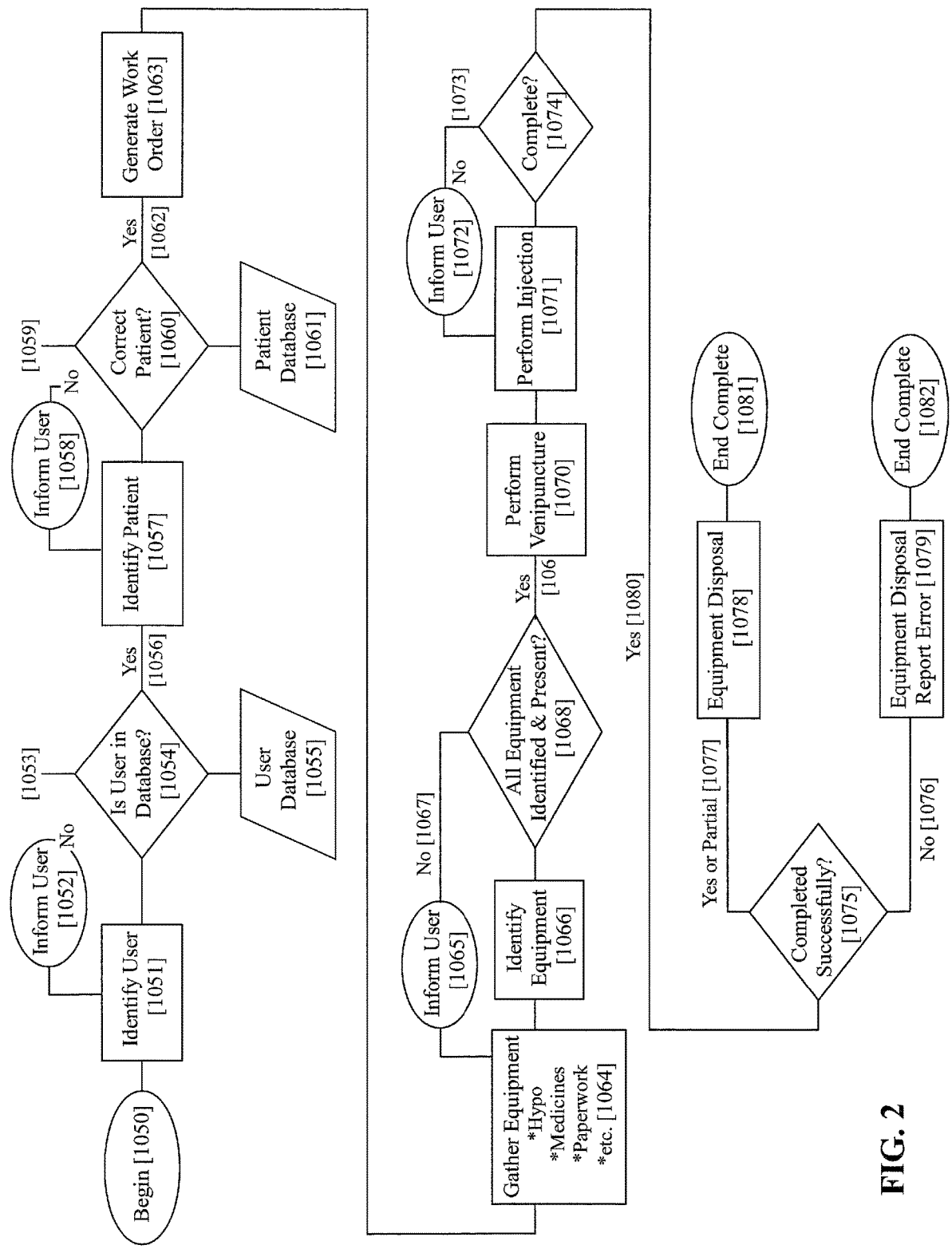
FIG. 2—this flowchart describes the process for injecting medicines into a patient using an embodiment of the invention that combines vein location with other data collection including biometrics and bar code scanning.

In addition, an enhanced scanner ban assist in the management of the injection process in a similar way as described above for taking blood specimens. Referring to FIG. 2, a substantially similar process is presented. Steps 1050-1069 are handled as previously described for steps 1000-1019 in FIG. 1. While blood draw is typically handled with a single catheter and multiple containers, injections might use multiple hypodermics, so step 1070 is not always performed and step 1071 might include multiple injections and therefore multiple uses of the scanner to verify vessel location. All of the remaining steps are substantially identical to that described above.

Intramuscular Injections

A primary focus of the invention has been to locate blood vessels so that a practitioner can access that vessel with a needle for withdrawing blood or injecting a material into the blood stream. In medical practice, some inject-able substances must be injected into the muscle rather than into a vein. Through the use of the invention, veins can be located for this procedure and the area between veins can be targeted by the practitioner thereby reducing the risk of inadvertently injecting the substance into a vein.

Image Capture

In an embodiment of the invention where the laser is scanned in a predictable and repeatable pattern, such as a raster pattern, an image of the targeted area can be captured and stored into memory. This image can be of sufficient quality and resolution to allow image processing techniques that are well known in the art to be applied to this captured image.

As previously described, this stored image can be used for many purposes such as using various image processing techniques to find the vein pattern within the image. In addition to the location of the vein, with appropriate image processing software the scanner can be used to capture and present additional information about objects seen in the field of view.

In a digital camera a photo detector array that has elements that are separately sensitive to red, green and blue light are used with either ambient light or a broad spectrum white light to capture the image. In a laser based system, the image being captured is based on the target surface's reflection of the light of the specific color (wavelength) of the laser being projected.

For each laser used in the system an additional color can be captured and included in the image. In the preferred embodiment with an infrared and a visible red laser, an image can be captured based on both the reflectivity at infrared and red. Depending on the desired result, one or both of these images can be used. For example, in a bar code application, a bar code could be scanned with the infrared laser that is invisible to the human eye. With the addition of other color lasers, more information about the target surface can be captured.

Finding Needle

Since the needle is a large object that is above the surface of the body prior to venipuncture, image processing software can be used to identify the position of the needle using its different characteristics when compared to skin and sub-skin body parts. Since the invention both captures an image and projects an image, the user can be prompted with projected feedback as to the position of the needle in relation to the nearest vein in the field of view. Since it is important that the needle pierces the vein in its center, icons such as cross hairs or arrows can be used to guide the practitioner to the proper position. For example, right/left/forward arrows can be used to accurately guide the practitioner to the center of the vein by showing them the direction to move the needle. The invention is also able to use other feedback mechanisms such as audible feedback or that of projecting text into the field of view with prompting information.

Finding Vein

Once the image is captured from the penetrating infrared laser, many algorithms well known in the art can be used to find the veins. Several things are typical in the types of veins that one would wish to select for venipuncture, including that it has a sizeable segment that is linear. Therefore, a line detection algorithm can be used. Another thing that is characteristic of the vein image being captured is that there are edge boundaries between the area surrounding the vein and the vein itself. An edge detection algorithm such as the one described by Canny in the IEEE Transactions on Pattern Analysis and Machine Intelligence archive, Volume 8, Issue 6 (November 1986), Pages: 679-698, Year of Publication: 1986, ISSN: 0162-8828, can be used to find these edges.

Finding Depth

In a preferred embodiment, the output intensity of the laser (or the gain of the photo detection circuitry, or a combination of both) can be varied from frame to frame as the scanner passes over the target area. The higher the intensity, the deeper the laser will penetrate the body. At a low setting, the veins identified will be close to the surface. At higher settings, more and deeper veins will be identified.

By comparing the images between frames a determination can be made of which veins are close to the surface of the body and which veins are deeper. As the intensity increases and new veins become visible, the image processing software can tag the veins seen with an indicator of the intensity at which they first became visible. This provides an indication of relative depth.

Several user interfaces are possible. In a system with multiple, differently colored projection lasers, veins at different depths can be displayed in different colors. In a system with a single projection color, the lines that represent the veins could have patterns superimposed over the vein to indicate depth such as crosshatching for shallow and solid for deep. An alternative embodiment would be to allow the user to set what depth to look at so that only the veins of a specific depth are presented to the user.

Bar Code

There is a significant body of knowledge on the use of image capture devices to read bar codes such as described U.S. Pat. No. 6,223,988. Since the invention is capable of capturing an image of the necessary resolution and quality for bar code detection, algorithms well known in the art can be used to find and decode bar codes that are in the field of view.

Bar codes are commonly used to identify users (through ID cards or badges), identify patients (through wrist bands) and to identify equipment (through bar-coded labels) in medical environments. It is an important extension of the invention to have it able to read bar codes so that it can be fully integrated into the work flows of the medical environment.

Figure 3:
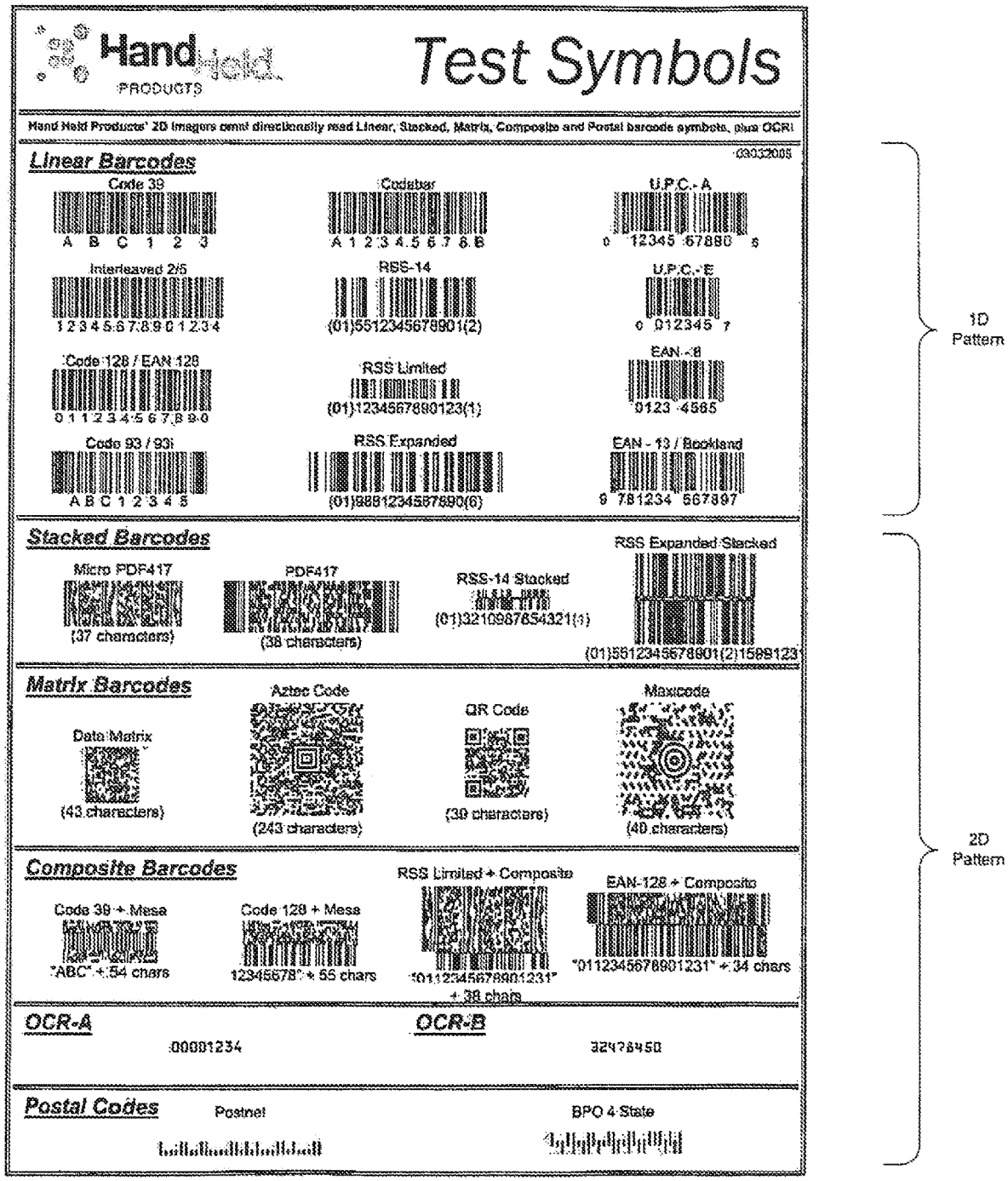
FIG. 3—this exhibit shows the types of bar codes that might be used in the invention FIG. 4—this drawing shows examples of text and icons that might be projected by the engine.

The invention can be implemented such that it captures images of the field of view, and stores those images into computer memory. Using techniques well known in the art, the captured images can be searched for the presence of bar codes such as those shown in FIG. 3. Both the 1D and 2D bar codes shown in FIG. 3 could be captured by an image capturing version of the invention. An alternative version of the invention can use the signal from a single line of the laser scanning pattern, as it crosses a 1D bar code as seen in the upper portion of FIG. 3, and decode the bar code through the reflections of the marks and spaces through techniques that are well known in the art.

By re-using the image capture capabilities of the scanner for bar code reading a very small, tightly integrated, low cost embodiment can be created that combines vein location and bar code scanning.

An alternative implementation of bar code scanning would be to use a commercially available off the shelf bar code scanning engine such as those available from Hand Held Products integrated into the housing of the invention. This would have the advantage of keeping the vein detection portion of the design simpler and forgo the need to develop or integrate bar code reading into the vein detection electronics and software. The disadvantage is that there would be redundancies that might increase the size and cost of the unit.

Biometrics

As previously described, the ability to identify the user of the invention and the patient upon which the invention will be used are very useful to the management of the medical procedures. Simple methods of passwords or PINs can be used for the user identification, and as previously described bar coded wrist bands can be used to identify the patient. However, each of these approaches has its weaknesses in that the password or PINs can be misplaced and the wrist band is only available in a hospital environment.

Once again, the image capture capabilities of the invention can be used for capturing many biometric identifiers such as but not limited to fingerprint, face recognition, iris or retina recognition, and vein pattern recognition through techniques well known in the art.

There are many biometric capture devices available on the market that are designed to be integrated into an OEM devices such as laptops. This includes fingerprint modules such as those available from AuthenTec (www.authentec.com) which can be integrated into the invention. This avoids the complexity of the user having to 'take a picture' of their finger and allows them to simply swipe their finger on the sensor.

While fingerprint has become a common method of biometric identification, any biometric identification device could be integrated into the invention to allow the user and patient to be identified.

Non contact biometrics can be valuable in a medical situation. For example, a fingerprint would be difficult to read from the gloved hand of the practitioner and the device would have to be cleaned between patients if they came in physical contact with it for a fingerprint swipe. Therefore, non contact biometrics are very desirable. By adding a microphone and associated analog to digital circuitry, sound sampling can be included in the invention and voice recognition techniques well known in the art can be applied to user and patient identification.

Non-Linear Scanning Speeds

The scanning speed of a moving laser and the resolution of the captured image are subject to many physical limitations such as the maximum speed of the mirror, and the bandwidth of the electronic circuitry. However, it is desirable in some embodiments to have a higher resolution of the image on a particular area of the body than the device is inherently capable of. One mechanism to overcome this limitation would be to reduce the area being scanned so that whatever the native resolution of the device is, it is being applied to a smaller physical area. This trades off scanning area vs. resolution.

An alternative embodiment of the device would is to change the resolution of the scanned image in a particular area of the field of view. For example, since the practitioner would typically focus their attention on the center of the field of view, if the device can be made to have higher resolution at the center, the information content of the projected image would be higher at that most important point, without reducing the total field of view of the device. In a scanned laser implementation, this is done by varying the amplitude of the drive circuit so that the mirror moves less quickly in the center and more quickly outside of the center. The increase in dwell time at the center of the image provides higher resolution in that area. The decrease in dwell time outside the center would reduce the resolution in that area. The advantage of this over the previous embodiment is that the total field of view is maintained while sill gaining an improvement in resolution of the targeted area.

Business Models

Most medical practitioners will have the need to draw blood or otherwise stick the patient in their normal course of practice. However, for many of these practitioners this is not done on a regular basis. For example, in a general practitioners office this might be only two to three times a day. This presents a dilemma. On one hand, they don't do the procedure often enough to become very skilled, and would therefore gain an extraordinary benefit from a vein location device, but on the other hand they don't perform the procedure often enough to cost justify the acquisition of such a device.

Records of usage can be:
1. Uploaded immediately through a wireless connection
2. Kept in the device memory and then uploaded to a billing system later through a wired or wireless connection
3. Kept in the device on a removable storage device such as an SD card and then transferred to a billing system by removing the card from the device
4. Entirely within the device by using a pre-paid billing approach where a certain number of usages are enabled and the device counts down until there are none left and then disables itself until such a time as more credit is added, through a wired, wireless or physical token as discussed above.

To overcome-this dilemma, the device can be modified to provide a per use-type licensing model. This can be approached by keeping track of the number of times the device is activated in memory that is built in to the device. Various schemes can be used to activate the device such as:
1. Enable the device for a pre-determined period of time. This can be cheated in that there is no limit to the number of patients scanned during that period of time.
2. Enable the device for an unlimited period of time after a particular patient is identified through a biometric scan such as vein pattern, face or voice recognition. This is more expensive to implement, but is much harder to cheat.
3. Some combination of 1 and 2.

The inverse of this dilemma is an office with many practitioners where they share the device. In such a circumstance, the benefit of the device is very large when the entire group is considered. It would desirable to be paid more for the device in such a circumstance. Through the use of biometrics, the practitioner can be identified and a record can be kept in the device of that practitioner's access of the device. As above, various schemes can be used to activate the device such as:
1. Enable the device for a pre-determined period of time. This can be cheated in that there is no limit to the number of patients scanned during that period of time.
2. Enable the device for an unlimited period of time after a particular patient is identified through a biometric scan such as vein pattern, face or voice recognition. This is more expensive to implement, but is much harder to cheat.
3. Some combination of 1 and 2.

Data Collection

In the simplest embodiment, a vein scanner is a stand alone device that simply detects and projects a vein pattern back on to the skin of the patient. In this embodiment, no data about the process or the patient is retained for future use. In an enhanced embodiment, the device can be used to collect, store, manipulate and transmit information about the user, the usage of the device, and the patient. Also, updated control software and firmware can be uploaded to the device. In addition, data can be transferred into the scanner that can be used as previously described to manage the processes associated with venipuncture.

The transfer of information can either be batched up so that when needed the device can be connected to a computer system for upload and download, but in normal operation it is unconnected, or the device can be always connected to a computer system either through a wired or wireless connection. There are advantages and disadvantages and costs associated with each of these techniques that are well known.

While a bi-directional connection that allows the systems to acknowledge that communications have been properly received, a one-way communication scheme can be used for simple embodiments.

Wired Connectivity

The device can be connected to a computer system using a cable such as commonly seen in bar code scanners at store checkouts. The advantage of this implementation is that it is typically low cost and doesn't require that a battery be in the handheld and eliminates the need to charge the battery. The disadvantage is that the unit cannot be moved far from the computer and the cable can get in the way and easily breaks. Approaches well known in the art can be used for cabled communication such as RS232, USB or Ethernet can be used for transport medium.

Wireless Connectivity

A wireless implementation eliminates the problems associated with, a cable with the tradeoff that a battery is needed in the device. Wireless can be implemented with well understood approaches such as point-to-point proprietary protocols such as seen in remote control key fobs or standard protocols such as Bluetooth or WiFi.

Optical Connectivity

Since the device contains both a means of measuring light with its photo detector and emitting light with its lasers, these devices can also be used to transmit and receive data. Thorough the use of modulation schemes that are well known in the art, the laser can be used to transmit data to a remote receiver that could be integrated into the cradle or into a stand alone receiver. This receiver would have a photo detector system capable of detecting and decoding the modulated laser light. It would also have an output system such as a LED or LEDs that would transmit a modulated light signal at a wavelength that can be detected by the photo detector in the handheld. In this manner a two-way communication session can be established.

Batch Connectivity

Memory can be added to the system so that system events can be captured and system control information can be kept in that memory. From time to time, the information collected will need to be sent to another computer or new control information will need to be downloaded to the scanner. Any of the communication techniques previously described can be used on an ad-hoc basis to connect the scanner to a computer and to transfer the information. When not transferring information, the scanner is disconnected from the computer system and continues to operate in a stand alone mode.

Flashlight

In many field medical situations, there is limited ambient light available for performing procedures such as venipuncture. One mechanism that a practitioner would use to improve lighting would be to use a handheld flashlight to illuminate a specific area of the patient's body. One embodiment of the invention would be to integrate the scanning capability into a flashlight and the inverse of integrating a flashlight into the device.

One embodiment is that the invention be used such that the intensity of the projected field is bright enough to illuminate the body area without the need of additional lighting during the venipuncture process. This can be implemented so that the intensity is controllable by the user with the same hand that is holding the scanner. By varying the intensity of both the dark areas that represent veins and the light areas that represent the spaces between veins, and keeping the contrast between the two sufficiently different, the field of work can be kept well lit while maintaining the ability to discern the vein positions.

Integrated Scanner Into a Flashlight

Most of the embodiments of the invention have been described as stand-alone devices. However, since the scan engine of the invention can be miniaturized, it is uniquely suited to be integrated into other devices already in use by the practitioner. For example, the scan engine can be built into an otoscope such that it becomes a multi-function device for both looking into shaded areas of the body such as the ear canal and then used for vein location. The advantages to the user are that they have a single device to buy and manage and a single battery can be used.

Another device that the invention can be integrated with is a flashlight. Depending on the application, the scanner can be integrated so that the light beam and the scan/projection field are aligned along the same path. In this manner, the area of the body is illuminated by the flashlight and the vein pattern is viewable in the same field. The laser projection will be bright enough for most applications, but the flashlight/scanner combo can contain controls that alternately switch between scan/project only, light only and both or other combinations of those modes. The intensity of both the flash light and the projector can be controlled in these modes to ensure that the pattern remains visible without becoming over-bright or too dim.

Integrated Flashlight Into the Scanner

An alternative approach is to add lighting capabilities to the scanner. Finer control over the modes of the device can be accomplished in this way. In a preferred embodiment, the scanner is implemented so that multiple lasers allow any color to be projected on to the body including white. In this way, the field of view can be illuminated in white light and the other colors can be used to identify the position of the veins and to project data into the field of view. Since there is no competing illumination from a flashlight bulb, the image will be easier to read, while still illuminating the body part.

A further enhancement of the invention would be to implement a non-linear scanning pattern so that the illuminated area can be made arbitrarily wide, thereby increasing the device's utility as a flashlight while maintaining a good vein image in the center of the scan area.

A user interface can be implemented that allows the practitioner to switch between these modes and to modify the parameters such as intensity, field of view and field of high resolution. This user interface can be either controls for user input or based on the distance to the target area or both.

Telemedicine

The use of robots to provide fine control of surgical tools is well known in the art. In U.S. Pat. No. 7,155,316, a robot system for use in surgical procedures is described. In U.S. Pat. No. 7,158,859, a mobile robot that provides the ability to remotely control the robot and to see the patient, the patient surroundings and the tools in use is described.

In a normal patient encounter for venipuncture, the practitioner would use several senses to locate a vein and then to perform venipuncture. This would include looking for both visible and tactile indicators of the vein position. The invention enhances the visible feedback of the position of the veins. By using the visual position enhancement, the ability to use a tele-robot to perform venipuncture is enhanced.

The vein scanner engine can be integrated into one of these robots so that the scanning/projection field is positioned in alignment with the end of a robotic arm which contains the needle or catheter for the venipuncture procedure. The engine can be mounted directly to the arm that contains the needle or it can be mounted to a separately controllable arm.

The engine can work in one of three modes. It can work as it normally does such that the acquisition of the vein pattern and the projection of the vein pattern is directly on the patient's skin. In this mode, the cameras that are already on the robot can view the pattern on the skin and send that back to the remote operator on the screen that is already provided for the remote operator.

In a second mode, the detected vein pattern is captured and then rather than projecting the pattern back on to the patient, the pattern is sent to the remote practitioner and is shown to them on a screen. In this mode, there are several possible embodiments. One is that the pattern of veins can be overlaid on the video display of the patient's body. In this manner, what they see on the screen is very much like what they would see on the body. The advantage of this is that the image from the vein scanner can be enhanced and made brighter than it would be in the first mode.

In a third mode, a combination of the first two modes can be used that allows the practitioner to switch between the modes or for both modes to be used simultaneously on two different screens or windows on a single screen.

Figure 7A:
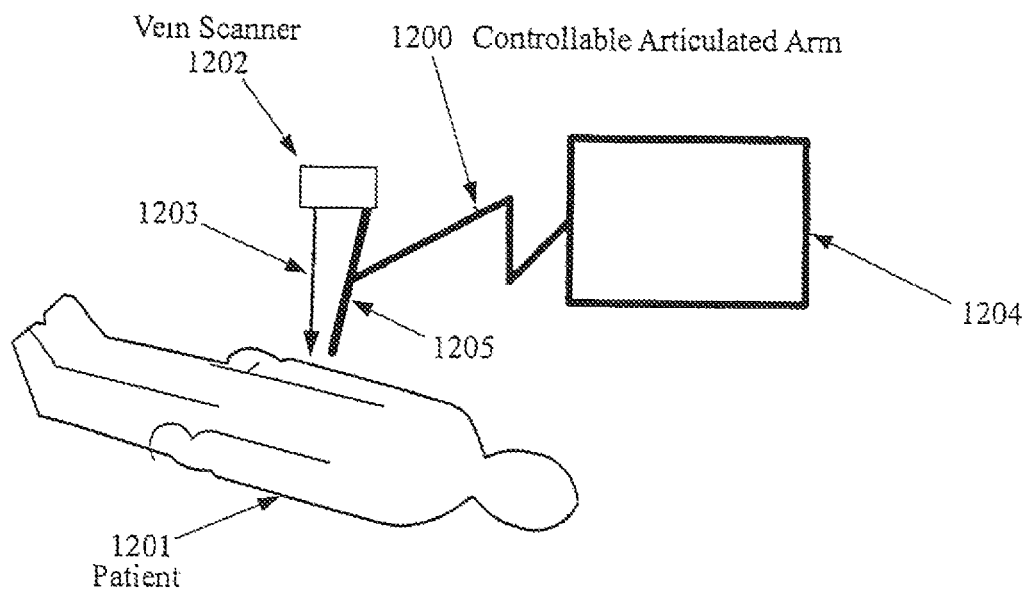
FIG. 7A—this drawing shows how the device can be integrated into a robotic system.
Figure 7B:
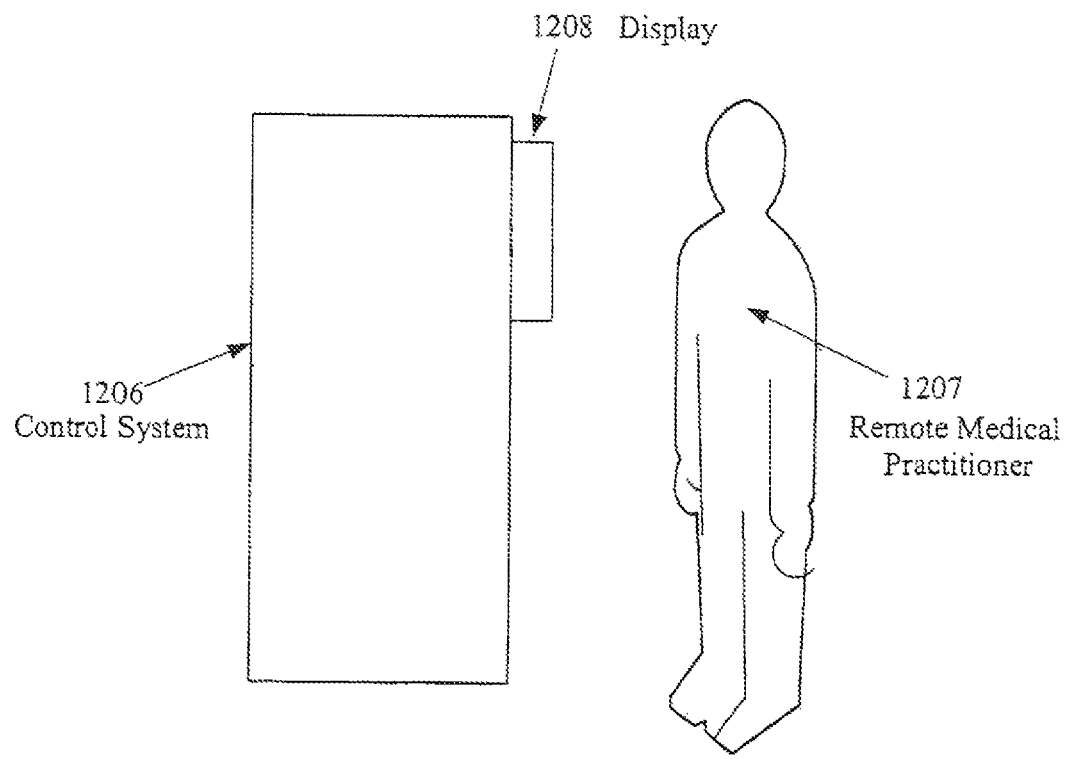
FIG. 7B—this drawing shows the robotic control system of FIG. 7A, with a display and a control system.

Referring to FIGS. 7a and b, a robotic control system 1204 is shown with a controllable articulated arm 1200 holding a medical device 1205. The remote medical practitioner 1207 uses a corresponding control system 1206 to move the arm 1200 and the medical device 1205 to perform a medical procedure on the patient 1201. The remote system 1206 has a display 1208 that the practitioner uses to view the patient 1201 and the action of the medical device 1205. Typically this is performed by a camera mounted to the medical device 1205 or to the arm 1200. Our invention adds a vein scanner device 1202 to either the medical device 1205 or the arm 1200. The vein scanner is arranged in such a way that the scanned area overlaps in a known orientation with the medical device. In a preferred embodiment the medical device is a syringe and the enhanced vein pattern is used to properly position the syringe for venipuncture. The invention enables this by either projecting the pattern on the patient's body such that it is viewed by the camera and seen by the practitioner on the remote display 1208 or alternatively a second display is mounted along with the camera display 1208 so that a digital version of the vein pattern can be seen or alternatively a single display is used with the digital version of the vein pattern overlaid over the camera view of the patient.

Non Contact Photoplethysmography

Pulse oximetry is a non-invasive method of measuring arterial oxygen saturation. The use of an infrared light source and a red light source along with a photo detector in a finger clip arrangement to measure pulse and oxygen levels in blood are well known in the art. The basis for the measurement is the differential absorption between oxygenated hemoglobin and non-oxygenated hemoglobin of the two different wavelengths of light. The traditional technique for performing this measurement requires contact with the body and relies on the transmission of the light through an area of the body with a small cross section such as a finger or an earlobe. By alternating between the red and infrared light sources and measuring the level of the light that is passed through a body part, a waveform that is known as a photoplethysmograph (PPG) is captured. Through signal processing techniques that are well known in the art, oxygenation levels and pulse rates can be calculated.

Several articles and patents have been published that use non-contact techniques to measure the necessary waveforms by replacing the photo detector with a remote device such as a CMOS camera. U.S. Pat. No. 6,491,639 describes the use of a light sources and the photo detector in the same plane eliminating the need for a small cross section part of the body to be used for measurement of the necessary waveforms. This design relies on the internal reflections of the body such that the light is directed in to the body and then reflected out of the body rather than completely passing through a small cross section portion of the body.

In the article by Humphreys, K. et al, "A CMOS Camera-Based Pulse Oximetry Imaging System." Proceedings of the 2005 IEEE Engineering in Medicine and Biology 27th Annual Conference (2005). 7 Feb. 2007, they describe a non-contact pulse oximetry system that uses a CMOS camera as the detector. In this design, the detector is held at a distance from the body and a bounding box is selected in the captured image. The average intensity of the bounding box is used as a proxy of the photo detector value that would be found in a contact pulse oximeter. By plotting the changing value of the average intensity of that location over time a PPG is derived that can be used to measure oxygenation and pulse using the same techniques as previously described.

Our micro vein enhancer invention uses scanned lasers to capture a pattern of veins below the surface of the skin and then re-projects a vein pattern image directly back on to the body. In one embodiment those laser light sources are visible red for projecting the image and infrared for detecting the veins. The vein detection relies on absorption characteristics that are related to those used in pulse oximetry in that the infrared light is absorbed differentially by hemoglobin than surrounding tissues.

Furthermore, we have previously described how a micro vein enhancer can be used to capture images based on the light transmitted by the lasers and reflected back to the micro vein enhancer's photo detector circuitry. Through the combination of these techniques, a miniature vein enhancer can be extended to read pulse and oxygen levels without contact with the patient.

Referring to FIG. 6a, view of the body surface 1150 is being illuminated by the scanning laser pattern 1160. Since information must be collected separately from each laser wavelength, a mechanism is required for the system to differentiate the reflected energy from each laser. One mechanism is to use optical filters and two photo detectors, each responsive to only one of the lasers. Another mechanism is to polarize the lasers so that two photo detectors, each sensitive to only one of the laser's polarization.

A further mechanism is to project using both the visible red and infrared lasers in an alternating pattern. The alternation can be handled in multiple ways. Possibilities include the lasers time sliced so that short pulses of each laser are alternated while the laser scans. Alternatively, the lasers can be switched between scan lines with right to left with one laser and left to right with the other laser. Alternately, the lasers can be switched on some multiple of scan lines or on alternate complete passes of the scan area.

Referring to FIG. 6b, a part of the body 1153 is illuminated by the scanning laser pattern 1154 from the vein enhancer. Portions of the laser light are reflected and absorbed off different structures of the body. The portion that is reflected 1155 is measured by the photo detector of vein enhancer. The laser projects a point source on to the body. Therefore the reflected signal is characteristic of a small area of the body. Since the PPG needs to be representative of both venous and arterial blood, the small point source reflection may be insufficient for detecting the PPG.

Referring back to FIG. 6a, the scanned area 1160 is broken down in to a number of smaller areas (e.g., 1151/1152) that are sized to capture a large enough area of the body such that an adequate PPG can be detected. The system can dynamically change the size of the smaller areas such that they are sufficiently large to obtain an adequate return signal regardless of the distance of the scanner from the body. The system then averages the returned signal from all of the pixels in the smaller areas and records the values. By keeping track of these values for the same location, over time, a PPG is generated.

Since the preferred embodiment is a handheld device, the motion of the device in relation to the patient must be allowed for. In the simplest embodiment, since the device is breaking the scan area down into a series of subsections and generating the PPG from the subsections and there would be similar return signals from these subsections, the motion can be ignored. However, if the motion becomes too severe or if the area being imaged is heterogeneous, then the system can use digital or optical image stabilization well known in the art to maintain alignment from frame to frame. An alternative method would be to keep PPGs from all of the subsections, then as the hand moves, the system would use the PPG from areas that still remain in view.

Non Contact Pulse Measurement

Many commercially available exercise machines such as treadmills and bicycles provide the capability to measure pulse rate. Knowledge of the current pulse rate is very valuable for managing excursive intensity. One commonly seen embodiment relies on hand contact with electrodes that are used to measure heart rate. In many situations, such as running, it is difficult or dangerous to maintain contact with the electrodes. Another common embodiment uses a chest strap that measures heart rate and then wirelessly transmits it to the exercise machine so that the value can be displayed. This requires that the user acquire this separate device in order for pulse rate to be displayed. In a preferred embodiment of the invention, a capture only scan engine is mounted in proximity to the user such that the scanning pattern is oriented such that it strikes an uncovered portion of the body such as the hands, arms, neck or face. As described previously, the PPG waveform can be captured and the pulse rate can be fed back into the exercise machine and displayed to the user.

Figure 8:
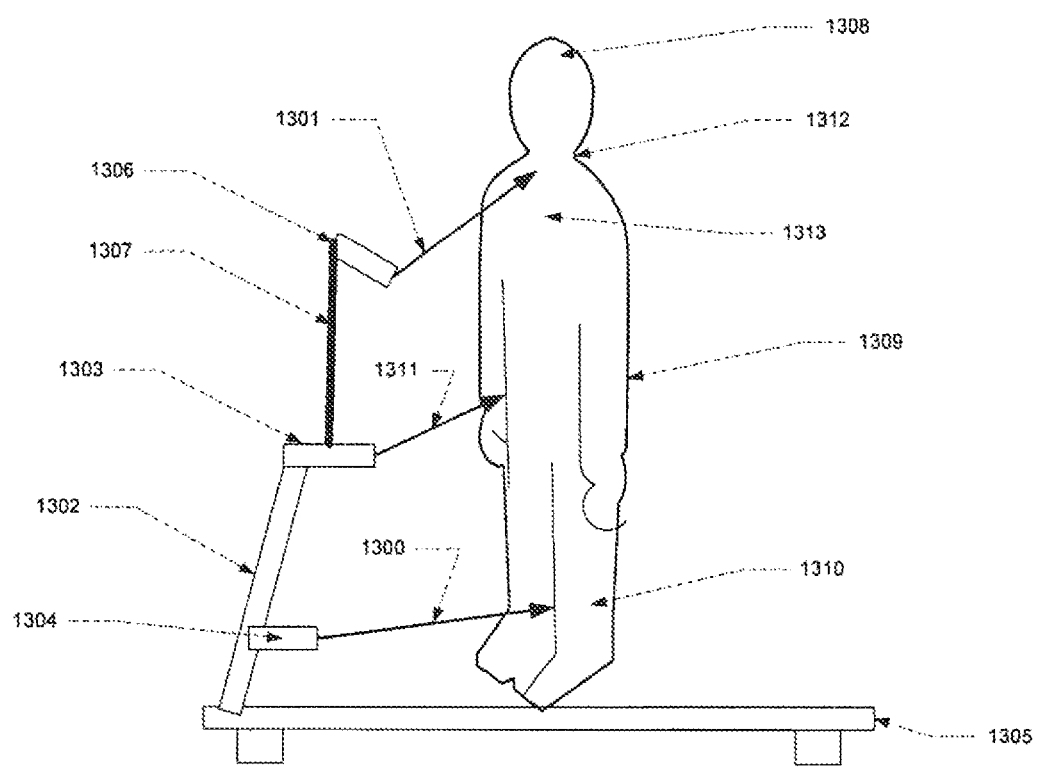
FIG. 8 shows a person on a treadmill using the invention.

Referring to FIG. 8, a person is shown exercising on a treadmill. A typical treadmill is composed of the bed 1305 which houses a moving belt, an upright 1302 at the front of the treadmill and a combination control panel, display panel and handle at 1303. The invention needs access to bare skin and therefore needs to be mounted in proximity to typically uncovered locations such as the legs 1310, the arms 1309 or the neck 1312 and head 1308. In addition, to normally uncovered body parts during exercise, in some embodiments it would be desirable for the torso 1313 to be bare or for a shirt made from materials that are transparent to the wavelength of the scanning light to be worn. Various embodiments of the invention can have at one or more of locations including a laser scanner engine 1304 mounted on the treadmill upright 1302, or an engine mounted in the display panel 1303. In addition, an additional upright 1307 can be added to the treadmill to allow for a scanner engine 1306 to be mounted above the standard parts of the treadmill. Given that the person will typically be moving, it is preferred that the scanner target a part of the body that moves the least. Therefore, the preferred embodiment would target the upper part of the body rather than the legs or the arms. Given that the pulse measurement application requires much lower resolution than the projector application described elsewhere, the full travel of the moving mirror can be used to steer the measurement zone over a fairly wide range of locations. This agility provides two benefits. One, the beam can be steered to the general desired location and the beam can be moved in synchrony with the movement of the body during exercise. Beam positions 1300, 1311 and 1301 show nominal center points for the beam. However, they can be steered in real time as desired within the general area of the center point.

We claim:

1. A portable handheld vein-image-enhancing device configured for single-handed use by a practitioner in the performance of a venipuncture procedure through: imaging of subcutaneous veins of a target area of a prospective patient, biometric identifying and verifying that the prospective patient is an actual patient scheduled to undergo the venipuncture procedure, and projection of the imaged veins onto the target area to assist the practitioner during the venipuncture procedure, said portable handheld vein-image-enhancing device comprising:
a first light source configured to emit a first wavelength of light;
one or more optical detectors, said one or more optical detectors each configured to be responsive to said first wavelength of light, to receive an image of a vein pattern of the prospective patient formed by differential amounts of absorption and reflection of said emitted light at said first wavelength by the subcutaneous veins and surrounding tissue; said one or more optical detectors further configured to convert said vein pattern image into a signal;
electronic circuitry, said electronic circuitry comprising: a memory;
a database stored in said memory, said database comprising: a plurality of vein patterns of a corresponding plurality of known patients;
wherein said electronic circuitry is further configured to compare said received vein pattern image of the prospective patient to one or more of said plurality of vein patterns stored in said database, to verify said received vein pattern image is a match for the actual patient;
a housing, said housing configured to permit single-handed lifting and use of said handheld vein-image-enhancing device during handheld imaging of the target area;
a second light source configured to emit a second wavelength of light, being different than said first wavelength of light;
wherein said second light source is further configured to receive said signal and to project said received vein pattern image onto the target area to overlay the subcutaneous veins of the target area.

2. The portable handheld vein-image-enhancing device according to claim 1, further comprising a biometric identification device configured to cooperate with said electronic circuitry to redundantly verify that said received vein pattern image is a match for the actual patient.

3. The portable handheld vein-image-enhancing device according to claim 2, wherein said biometric identification device comprises a fingerprint reader device.

4. The portable handheld vein-image-enhancing device according to claim 2, wherein said biometric identification device comprises a face recognition device.

5. The portable handheld vein-image-enhancing device according to claim 2, wherein said biometric identification device comprises a retina recognition device.

6. The portable handheld vein-image-enhancing device according to claim 2, wherein said biometric identification device comprises a voice recognition device.

7. The portable handheld vein-image-enhancing device according to claim 1, further comprising a card reader configured to cooperate with said electronic circuitry to read a user identification card to verify a valid user of said device.

8. The portable handheld vein-image-enhancing device according to claim 1, further comprising a key pad configured to cooperate with said electronic circuitry to read an inputted pass code to verify a valid user of said device.

9. A portable handheld vein-image-enhancing device configured for single-handed use by a practitioner in the performance of a venipuncture procedure, said device comprising:
means for generating an image of a vein pattern of a target area of a prospective patient using an infrared wavelength of light;

means for converting said vein pattern image into a signal;

electronic circuitry, said electronic circuitry comprising: a memory;

a database stored in said memory, said database comprising: a plurality of vein patterns of a corresponding plurality of known patients;

wherein said electronic circuitry is further configured to compare said vein pattern image to of the prospective patient to one or more of said plurality of vein patterns stored in said database, to verify said received vein pattern image is a match for an actual patient scheduled to undergo the venipuncture procedure;

wherein said portable handheld vein-image-enhancing device is configured to permit single-handed lifting and use of said handheld vein-image-enhancing device during handheld imaging of the target area;

a light source configured to emit a visible wavelength of light;

wherein said light source is further configured to receive said signal and to project said vein pattern image onto the target area.

10. The portable handheld vein-image-enhancing device according to claim 9, further comprising a biometric identification device configured to cooperate with said electronic circuitry to redundantly verify that said received vein pattern image is a match for the actual patient.

11. The portable handheld vein-image-enhancing device according to claim 10, wherein said biometric identification device comprises a fingerprint reader device.

12. The portable handheld vein-image-enhancing device according to claim 10, wherein said biometric identification device comprises a face recognition device.

13. The portable handheld vein-image-enhancing device according to claim 10, wherein said biometric identification device comprises a retina recognition device.

14. The portable handheld vein-image-enhancing device according to claim 10, wherein said biometric identification device comprises a voice recognition device.

15. The portable handheld vein-image-enhancing device according to claim 10, further comprising a card reader configured to cooperate with said electronic circuitry to read a user identification card to verify a valid user of said device.

16. The portable handheld vein-image-enhancing device according to claim 15, further comprising a key pad configured to cooperate with said electronic circuitry to read an inputted pass code to verify a valid user of said device.

* * * * *